United States Patent
Taniuchi et al.

(10) Patent No.: US 8,097,299 B2
(45) Date of Patent: Jan. 17, 2012

(54) ORGANIC RUTHENIUM COMPOUND FOR CHEMICAL VAPOR DEPOSITION, AND CHEMICAL VAPOR DEPOSITION METHOD USING THE ORGANIC RUTHENIUM COMPOUND

(75) Inventors: Junichi Taniuchi, Hiratsuka (JP); Masayuki Saito, Hiratsuka (JP); Minoru Ishida, Hiratsuka (JP)

(73) Assignee: Tanaka Kikinzoku Kogyo, Tokyo (JP)

( * ) Notice: Subject to any disclaimer, the term of this patent is extended or adjusted under 35 U.S.C. 154(b) by 933 days.

(21) Appl. No.: 12/091,782

(22) PCT Filed: Sep. 27, 2007

(86) PCT No.: PCT/JP2007/068805
§ 371 (c)(1),
(2), (4) Date: Apr. 28, 2008

(87) PCT Pub. No.: WO2008/044478
PCT Pub. Date: Apr. 17, 2008

(65) Prior Publication Data
US 2009/0238970 A1 Sep. 24, 2009

(30) Foreign Application Priority Data
Oct. 6, 2006 (JP) ................ P2006-275215

(51) Int. Cl.
*C23C 16/06* (2006.01)
*C23C 16/18* (2006.01)

(52) U.S. Cl. .............. 427/250; 427/255.28; 556/136; 106/1.05; 106/1.25; 106/1.28

(58) Field of Classification Search ............. 427/250, 427/252.2, 55.28; 556/136; 106/1.28, 1.05, 106/1.25
See application file for complete search history.

(56) References Cited

U.S. PATENT DOCUMENTS

| 5,254,742 | A * | 10/1993 | Ohgomori et al. ............ 568/463 |
| 6,207,232 | B1 | 3/2001 | Kadokura ................ 427/252 |
| 6,743,934 | B2 | 6/2004 | Saito et al. ................ 556/40 |
| 7,002,032 | B2 * | 2/2006 | Saito ................ 556/136 |
| 7,547,631 | B2 * | 6/2009 | Shenai-Khatkhate et al. ............ 438/680 |
| 2006/0177577 | A1 | 8/2006 | Thompson ................ 427/248.1 |

FOREIGN PATENT DOCUMENTS

| JP | 11-35589 | 2/1999 |
| JP | 2003-306472 | 10/2003 |
| JP | 2007-169725 | 7/2007 |

OTHER PUBLICATIONS

Ohgomori, Yuji et al., "Tail-To-Tail Dimerization Reaction of Acrolein". *Organometallics*, 1994, 13(10), pp. 3758-3760, Table 1.
Pertici, Paolo et al. "Synthesis of New Chiral ($\eta^4$-Arene) ($\eta^4$-diene)ruthenium(0) Complexes". *Inorganica Chimica Acta*, 1988, 149(2), pp. 235-239, Fig. 1, Scheme 2.
Bennett, Martin A. et al. "Dinuclear Arene Hydrido-Complexes of Ruthenium (II): Reactions With Olefins and Catalysts of Homogeneous Hydrogenation of Arenes." *Journal of the Chemical Society, Chemical Communications*, 1979, (7), pp. 312-314, Scheme 1.
Andreas Schneider et al., "[(1,5-Cyclooctadiene)(toluene)ruthenium(0)]: A Novel Precursor for the MOCVD of Thin Ruthenium Films". *Chemical Vapor Deposition* 2005, 11, No. 2, p. 99-105.

* cited by examiner

*Primary Examiner* — Matthew Daniels
*Assistant Examiner* — Dennis Cordray
(74) *Attorney, Agent, or Firm* — Roberts & Roberts, LLP

(57) ABSTRACT

The present invention is an organoruthenium compound for use in production of a ruthenium or ruthenium compound thin film by chemical vapor deposition, including ruthenium and an arene group and norbornadiene both coordinated to the ruthenium and represented by the following formula. The present invention is an organoruthenium compound for use in chemical vapor deposition which does not require the coexistence of oxygen during the thin film formation, and moreover, is liquid at ordinary temperature, thereby having good handleability and recyclability.

[Formula]

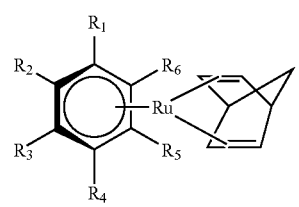

wherein the substituents, $R_1$ to $R_6$, of the arene group are each hydrogen or an alkyl group, and the total number of carbons of $R_1$ to $R_6$ ($R_1+R_2+R_3+R_4+R_5+R_6$) is 6 or less.

2 Claims, No Drawings

ORGANIC RUTHENIUM COMPOUND FOR CHEMICAL VAPOR DEPOSITION, AND CHEMICAL VAPOR DEPOSITION METHOD USING THE ORGANIC RUTHENIUM COMPOUND

TECHNICAL FIELD

The present invention relates to an organoruthenium compound which is used as a raw material for a ruthenium or ruthenium compound thin film produced by CVD or ALD. Particularly, the invention relates to an organoruthenium compound which is liquid at ordinary temperature, thereby having good handleability.

BACKGROUND ART

Ruthenium or ruthenium compounds have been used as a raw material for thin film electrodes of semiconductor devices such as DRAM and FERAM. Chemical deposition such as CVD (chemical vapor deposition) or ALD (atomic layer deposition) has been applied to the production of such thin films. And many organoruthenium compounds have been known as raw material compounds used in chemical vapor deposition. For example, bis(ethylcyclopentadienyl)ruthenium represented by the following formula is a compound most frequently used as such a raw material.

Patent Document 1: Japanese Patent Application Laid-Open No. 11-35589

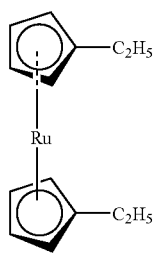

[Formula 1]

Many of previously known organoruthenium compounds, including bis(ethylcyclopentadienyl)ruthenium described above, require oxygen exists with them when they are formed into thin films so that they can be decomposed. Thus, in conventional thin film production, it is indispensable to introduce into the reactor oxygen, as a reactant gas, together with vaporized organoruthenium gas. However, in the thin film formation in the presence of oxygen, there is a fear that oxygen remains in the resultant thin film, causing the problem of deterioration in morphology and electric properties of the produced thin film.

Recently, there have been increasing demands for an organoruthenium compound which can be decomposed and formed into a thin film even in the absence of oxygen, and the application of (1,5-cyclooctadiene)(toluene)ruthenium represented by the following formula, as an organoruthenium compound as described above, has been considered. The organoruthenium compound including ruthenium and 1,5-cyclooctadiene, as a diene group, and toluene, as an arene group, coordinated to the ruthenium is a compound which can be decomposed by heating even in the absence of oxygen.

Non-Patent Document 1: Andreas Schneider et al., Chem. Vap. Deposition 2005, 11, No. 2, p. 99-105

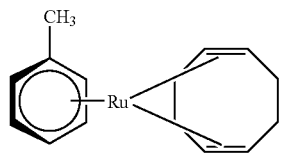

[Formula 2]

DISCLOSURE OF THE INVENTION

Problems to be Solved by the Invention (1,5-cyclooctadiene)(toluene)ruthenium described above is, however, solid at ordinary temperatures. Since a raw material compound is required to be vaporized in chemical vapor deposition, a solid raw material compound needs to be sublimed. However, chemical vapor deposition apparatus for liquid raw materials commonly in use cannot be used for this sublimation.

One of the possible measures taken to vaporize a solid raw material compound using chemical vapor deposition apparatus for liquid raw materials is to dissolve the solid raw material compound in an appropriate solvent. However, this method is not favorable, either. Making a solid raw material compound into a solution means diluting the raw material compound, and diluting the raw material compound means decreasing the amount of the raw material supplied to a reactor, and hence affecting the deposition rate. Furthermore, even if the raw material compound takes the form of a solution, the physical properties (e.g. melting point) of the compound itself do not change. Accordingly, the raw material gas generated by vaporizing the solution probably has a defect in its stability, which might cause the compound to be decomposed for example on the nozzles or valves of the deposition apparatus, and ruthenium to deposit on the same. Thus, using a solution of the solid raw material compound is not favorable, either, from the viewpoint of maintenance of the apparatus.

Further, a solid raw material compound has a problem of its recyclability. In recent years, it has been usual to recycle raw material compounds for use in chemical vapor deposition because their availability in a single deposition operation is low. The recycling is performed by trapping the exhaust gas from the reactor and recovering the unreacted compound in the gas; however, it is not easy to recover the solid compound by trapping the exhaust gas.

The present invention has been made in the light of the above background. Accordingly, the object of the present invention is to provide an organoruthenium compound for use in chemical vapor deposition which can be deposited to form a thin film even in the absence of oxygen as being a reactant gas, and which compound is liquid at ordinary temperature, thereby having good handleability and recyclability.

Means for Solving the Problems

The present invention, which solves the above described problem, is an organoruthenium compound for use in production of a ruthenium or ruthenium compound thin film by chemical vapor deposition, including ruthenium and an arene group and norbornadiene both coordinated to the ruthenium and represented by the following formula;

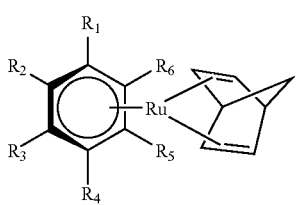

[Formula 3]

wherein the substituents, $R_1$ to $R_6$, of the arene group are each hydrogen or an alkyl group, and the total number of carbons of $R_1$ to $R_6$ ($R_1+R_2+R_3+R_4+R_5+R_6$) is 6 or less.

The organoruthenium compound of the present invention is characterized by having norbornadiene, as a ligand, coordinated to ruthenium. In the present inventors' knowledge, all the ruthenium compounds (complexes) having norbornadiene as a ligand are liquid at ordinary temperature and meet the requirement, handleability, for a raw material compound for use in chemical vapor deposition.

The organoruthenium compound of the present invention also has, as a ligand, an arene group (aromatic hydrocarbon) having substituents selected from the limited and prescribed range of substituent group. The substituents of the arene group are each hydrogen or an alkyl group and the total number of carbons of all the substituents is 6 or less. The reason the substituents of the arene group are selected from the limited range of substituent group is that the vapor pressure of the compound should be taken into consideration. For raw material compounds for use in chemical vapor deposition, which are used on the premise that they are vaporized, the magnitude of their vapor pressure is an important characteristic. For efficient thin film formation, a raw material compound having a high vapor pressure is preferably used. In the raw material compounds of the present invention, in the case that the arene group has more than 6 carbon atoms, their vapor pressure tends to be low, and hence they are unsuitable as compounds for use in chemical vapor deposition.

The substituents of the arene group should not be limited to any specific ones as long as they meet the above described requirements. Concrete examples of the organoruthenium compounds of the present invention include:

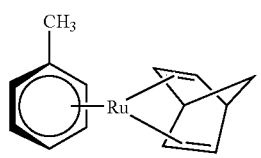

[Formula 4]

(Norbornadiene)(toluene)ruthenium; ($R_1$: methyl group, $R_2$ to $R_6$: hydrogen)

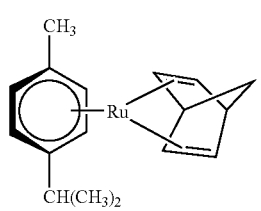

[Formula 5]

(Norbornadiene)(p-cymene)ruthenium; ($R_1$: methyl group, $R_4$: isopropyl group, $R_2$, $R_3$, $R_5$, $R_6$: hydrogen)

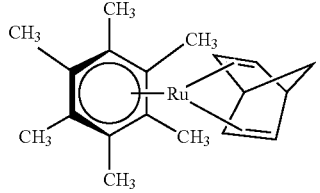

[Formula 6]

(Norbornadiene)(hexamethylbenzene)ruthenium; ($R_1$ to $R_6$: methyl group)

Of the organoruthenium compounds of the present invention, particularly preferable is (norbornadiene)(toluene)ruthenium, which is represented by Formula 4 above. (Norbornadiene)(toluene)ruthenium has the lowest molecular weight and the highest vapor pressure of the organoruthenium compounds represented by Formula 3, and therefore, it is particularly preferable as a raw material for use in chemical vapor deposition used in the vaporized state.

An organoruthenium compound of the present invention can be produced by using a ruthenium salt as a starting material and allowing the ruthenium salt to react with an arene group and norbornadiene one by one. Examples of ruthenium salts that can be used as a starting material include ruthenium chloride ($RuCl_3$). In the reaction of a ruthenium salt with an arene group, the reaction mixture is refluxed in an organic solvent at 70 to 120° C. for 4 to 6 hours. Preferably the reaction product is washed with an organic solvent. In the reaction of the ruthenium salt with norbornadiene, the reaction mixture is also refluxed in an organic solvent at 80 to 120° C. for 0.5 to 4 hours. Preferably the above sequence of reactions with an arene group and norbornadiene are carried out under an inert gas (e.g. nitrogen) atmosphere. The invention also provides a chemical vapor deposition process for producing a ruthenium or ruthenium compound thin film, comprising: vaporizing an organoruthenium compound, as a raw material compound, into a reaction gas; and heating the reaction gas while introducing the organoruthenium compound and the reaction gas onto the surface of a substrate, wherein the organoruthenium compound has the formula:

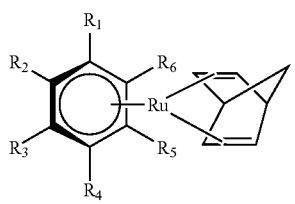

wherein the substituents, $R_1$ to $R_6$, of the arene group are each hydrogen or an alkyl group, and the total number of carbon atoms of $R_1+R_2+R_3+R_4+R_5+R_6$ is 6 or less.

BEST MODE FOR CARRYING OUT THE INVENTION

Example 1

In Example 1, (norbornadiene)(toluene)ruthenium, as the organoruthenium compound represented by Formula 4 above, was produced. Into a 5 L three-necked flask, 50.4 g of ruthenium chloride hydrate (ruthenium content: 39.6%), 2300 mL of ethanol and 52.1 g of 1-methyl-1,4-cyclohexadiene were introduced, and the reaction mixture was refluxed at 78° C. for 4 hours. The produced brown powder was filtered out, washed with 300 mL of methanol three times, followed by drying overnight in a vacuum drier to obtain 48.21 g of [Ru(toluene)Cl$_2$]$_2$. The yield of the product by this reaction was 92.5%.

Then, 15.9 g of [Ru(toluene)Cl$_2$]$_2$ produced by the above reaction, 82.8 g of sodium carbonate, 55.5 g of norbornadiene and 3000 mL of isopropanol were put into a 5 L three-necked flask, and the reaction mixture was refluxed at 81° C. for one hour. After the reaction, the reaction solution was filtered, the filtrate was heated to remove isopropanol and excess norbornadiene, and 1000 mL of hexane was added to the obtained residue to extract the necessary constituent. Then hexane was removed from the extract, and the extract was vacuum-distilled to obtain 7.75 g of (norbornadiene)(toluene) ruthenium, as a yellow liquid. The yield was 45.2%.

Example 2

In Example 2, (norbornadiene)(p-cymene)ruthenium, as the organoruthenium compound represented by Formula 5 above, was produced. Into a 5 L three-necked flask, 50.4 g of ruthenium chloride hydrate (ruthenium content: 39.6%), 2300 mL of ethanol and 306.6 g of α-phellandrene were introduced, and the reaction mixture was refluxed at 78° C. for 4 hours. The produced brown powder was filtered out, washed and dried in the same manner as in Example 1 to obtain 47.05 g of [Ru(p-cymene)Cl$_2$]$_2$. The yield of the product by this reaction was 77.4%.

Then, 18.4 g of [Ru(p-cymene)Cl$_2$]$_2$ produced by the above reaction, 82.8 g of sodium carbonate, 55.5 g of norbornadiene and 3000 mL of isopropanol were put into a 5 L three-necked flask, and the reaction mixture was refluxed at 81° C. for one hour. After the reaction, filtration of the reaction solution, removal of isopropanol etc., and extraction of the necessary constituent were performed in the same manner as in Example 1. After removing hexane from the extract, the extract was vacuum-distilled to obtain 7.44 g of (norbornadiene)(p-cymene)ruthenium, as a yellow liquid. The yield was 37.8%.

Example 3

In Example 3, (norbornadiene)(hexamethylbenzene)ruthenium, as the organoruthenium compound represented by Formula 6 above, was produced. Into a 2 L three-necked flask, 40.0 g of [Ru(p-cymene)Cl$_2$]$_2$ produced in Example 2 and 195.0 g of hexamethylbenzene were introduced, and the reaction mixture was refluxed at 180° C. for 4 hours. The obtained solid was washed with hexane and toluene and dried to obtain 37.6 g of [Ru(hexamethylbenzene)Cl$_2$]$_2$. The yield of the product by this reaction was 88.1%.

Then, 23.3 g of [Ru(hexamethylbenzene)Cl$_2$]$_2$ produced by the above reaction, 82.8 g of sodium carbonate, 55.5 g of norbornadiene and 3000 mL of isopropanol were put into a 5 L three-necked flask, and the reaction mixture was refluxed at 81° C. for one hour. After the reaction, filtration of the reaction solution, removal of isopropanol etc., and extraction of the necessary constituent were performed in the same manner as in Example 1. After hexane was removed from the extract, the extract was vacuum-distilled to obtain 9.57 g of (norbornadiene)(hexamethylbenzene)ruthenium, as a yellow liquid. The yield was 38.6%.

Of the organoruthenium compounds produced above, the (norbornadiene)(toluene)ruthenium of Example 1, which had a good yield, was measured for its physical properties pertinent to its chemical vapor deposition and tested for ruthenium thin film production. The physical properties of the compound were as follows.

TABLE 1

| Physical properties of (norbornadiene)(toluene)ruthenium | |
|---|---|
| Specific gravity | 1.52 (25° C.) |
| Viscosity | 71 cp (25° C.) |
| Vapor pressure | 1.0 torr (140° C.) |

Deposition test was conducted with a CVD apparatus equipped with a liquid source vaporization control system. Deposition conditions were as follows. Table 2 shows the evaluations of deposition rate under different conditions.

Precursor (raw material) feed rate: 0.1 g/min
Vaporizer temperature: 120° C.
Tape heater temperature: 150° C.
Ar flow rate through vaporizer: 500 sccm
Deposition temperature: 370, 400, 430, 460° C.
Deposition pressure: 0.1, 1, 5, 10 torr

TABLE 2

| | Deposition pressure | | | |
|---|---|---|---|---|
| | 0.1 torr | 1 torr | 5 torr | 10 torr |
| 370° C. | — | — | — | — |
| 400° C. | — | — | — | — |
| 430° C. | — | — | — | 0.6 nm/min |
| 460° C. | — | — | 0.4 nm/min | 2.4 nm/min |

* "—" means the film failed to be formed within 2 hours

It is apparent from Table 2 that in the deposition of (norbornadiene)(toluene)ruthenium, the deposition rate is improved by increasing the deposition pressure. This is because the partial pressure of the raw material compound is increased. The deposition rate is also improved at elevated deposition temperatures. Thus, efficient deposition is made possible by providing suitable deposition conditions.

According to the above Non-Patent Document 1, in deposition of (1,5-cyclooctadiene)(toluene), which is a conventionally used compound, by vaporizing the compound by sublimation method, the deposition rate is 0.28 nm/min. This value is lower than that of Example 1 described above, and deposition at such a low deposition rate cannot catch up with the demand for the thin film production on an industrial scale.

INDUSTRIAL APPLICABILITY

As described so far, the organoruthenium compounds of the present invention are liquid at ordinary temperature, and thin films of the same can be produced with a chemical vapor deposition apparatus, which has been applied to the production of thin films of conventional organoruthenium compounds such as bis(ethylcyclopentadienyl)ruthenium. Further, the compounds of the present invention themselves are liquid, and therefore, the reaction gas after vaporization is stable, and abnormal deposition is hard to occur on the parts of the CVD apparatus other than the reactor. Thus, the compounds are also favorable from the viewpoint of the maintenance of the deposition apparatus.

Further, the organoruthenium compounds of the present invention can be decomposed even in the absence of oxygen and formed into ruthenium thin films without a reactant gas. This means there remains no oxygen in the formed thin films, and thus, thin films having excellent morphology and characteristics can be produced.

The invention claimed is:

1. A chemical vapor deposition process for producing a ruthenium or ruthenium compound thin film, comprising: vaporizing an organoruthenium compound, as a raw material compound, into a reaction gas; and heating the reaction gas while introducing the organoruthenium compound and the reaction gas onto the surface of a substrate, wherein the organoruthenium compound has the formula:

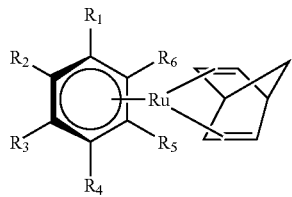

wherein the substituent, $R_1$, is a methyl group, the substituent, $R_4$, is an isopropyl group, and the substituents, $R_2$, $R_3$, $R_5$ and $R_6$, are hydrogen.

2. A chemical vapor deposition process for producing a ruthenium or ruthenium compound thin film, comprising: vaporizing an organoruthenium compound, as a raw material compound, into a reaction gas; and heating the reaction gas while introducing the organoruthenium compound and the reaction gas onto the surface of a substrate, wherein the organoruthenium compound has the formula:

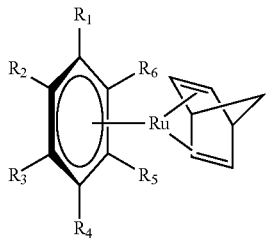

wherein each of the substituents, $R_1$ to $R_6$, is a methyl group.

* * * * *